United States Patent
Aeffner et al.

(10) Patent No.: US 10,504,224 B1
(45) Date of Patent: Dec. 10, 2019

(54) METHOD FOR DETECTING IMMUNOSTAINING BELOW THE THRESHOLD OF VISUAL PERCEPTION

(71) Applicant: Flagship Biosciences, Inc., Westminster, CO (US)

(72) Inventors: Famke Aeffner, Boulder, CO (US); Joseph Krueger, Andover, MA (US); Mirza Peljto, Louisville, CO (US)

(73) Assignee: Flagship Biosciences, Inc., Westminster, CO (US)

( * ) Notice: Subject to any disclaimer, the term of this patent is extended or adjusted under 35 U.S.C. 154(b) by 153 days.

(21) Appl. No.: 15/396,536

(22) Filed: Dec. 31, 2016

(51) Int. Cl.
*G06T 7/00* (2017.01)
*G01N 33/53* (2006.01)

(52) U.S. Cl.
CPC .......... *G06T 7/0012* (2013.01); *G01N 33/53* (2013.01); *G06T 2207/30204* (2013.01); *G06T 2207/30242* (2013.01)

(58) Field of Classification Search
CPC ......... G06T 2207/30024; G06T 7/0012; G06T 7/11; G06T 2207/30096; G01N 1/30
See application file for complete search history.

(56) References Cited

U.S. PATENT DOCUMENTS

| | | | | |
|---|---|---|---|---|
| 9,298,968 B1* | 3/2016 | Peljto | ............... | G06K 9/00127 |
| 9,784,665 B1* | 10/2017 | Milici | ............... | G01N 1/30 |
| 2011/0182490 A1* | 7/2011 | Hoyt | ............... | G06K 9/00147 382/128 |
| 2012/0076390 A1* | 3/2012 | Potts | ............... | G06T 7/0014 382/133 |
| 2012/0257811 A1* | 10/2012 | Metzger | ............... | G06T 7/0012 382/133 |
| 2013/0294676 A1* | 11/2013 | Parvin | ............... | A61B 5/0033 382/133 |
| 2014/0329716 A1* | 11/2014 | Kairdolf | ............... | G01N 33/574 506/10 |
| 2015/0004630 A1* | 1/2015 | Lange | ............... | G01N 33/5005 435/7.21 |
| 2017/0116734 A1* | 4/2017 | Van Leeuwen | ...... | G06K 9/0014 |

* cited by examiner

*Primary Examiner* — Utpal D Shah
(74) *Attorney, Agent, or Firm* — Josiah Barbour (57) ABSTRACT

The human vision is limited in terms of perception of color hues and intensities. Moreover, the individual's ability in this context varies greatly from person to person. Herein are described methods to quantify staining of tissue samples via digital tissue image analysis, when staining of a certain biomarker is below or at the threshold of human visual perception, in terms of saturation. This enables for consistent detection of these staining characteristics, which allows for more reproducible data generation through minimizing inter- and intra-observer variability.

12 Claims, 6 Drawing Sheets

METHOD FOR DETECTING IMMUNOSTAINING BELOW THE THRESHOLD OF VISUAL PERCEPTION

BACKGROUND

Field of the Invention

This application relates generally to methods for image analysis of tissue sections. More specifically, this application relates to extracting information from the immunostaining of a tissue section which has been assayed with a tissue-based test which detects the presence of a particular biomarker, where the immunostaining is at a level that is below or at the threshold of visual perception.

Description of the Related Art

Anatomic pathology, as a discipline, seeks to render a precise and complete diagnosis of lesions produced by a particular disease, to the correct patient, in a timely fashion, and in a way that is understandable and useful to the physician treating the patient. In a clinical setting, this definition is easily adaptable as an accurate and comprehensive diagnosis provided to the correct patient in a timely fashion and in a way that generates biologically meaningful data to benefit physicians. Such assessments usually include not just the diagnostic opinion but also a lesion score defining the severity, or grade, of the finding, as collective experience over time has linked such scores to clinical outcome.

In recent years, anatomic pathology diagnoses have evolved from a reliance on traditional manually acquired lesion scores to an increasing emphasis on automated tissue image analysis ("tIA"). The rationale for this shift is that manual scores are qualitative or semi-quantitative and subjective even when assigned by a seasoned observer, while tIA data is quantitative, reproducible, and objective. Analytical validation of tIA methods requires their comparison to an accepted reference standard, otherwise known as the "gold standard", which captures the actual understanding of what is happening, known as "ground truth". For tIA applications, the reference standard can be a similar modality that has been validated through extensive use (e.g., a manual histopathology score for the same tissue section) or an orthogonal (i.e., independent) methodology (e.g., quantitative PCR or western blot analysis of tissue from the same specimen). However, appropriate reference standards to validate novel tIA methods seldom exist in anatomic pathology practice. In nearly all cases, manual pathology scoring by a board-certified pathologist serves as the gold standard for anatomic pathology endpoints. Manual scores assigned by different practitioners may exhibit the same trend but are seldom identical; moreover, human fallibility is a well-known source of bias in manual scoring. These imperfections have been addressed by devising innovative digital pathology techniques, especially tIA, to overcome known pitfalls with manual scoring of biomarker expression by utilizing the strengths of anatomic pathologists (e.g., biomedical knowledge, cognitive abilities) to provide more reproducible data for making clinical decisions and for testing hypotheses in the translational environment.

In the field of validating tIA solutions, it is common practice that manual scores generated by a trained and experienced pathologist are used as a straightforward gold standard. The same stained tissues may be scored manually and then by tIA, after which the results may be compared directly to demonstrate equivalency between the manual and tIA procedures. Alternatively, an orthogonal modality may be used as the benchmark, but the need for different material degrades the contextual information (e.g., cellular localization) that is crucial for assessing biomarker expression in tissues. In either scenario, therefore, the nature of ground truth represents an informed choice.

While the number of colors that the human eye can distinguish continues to be elusive, published estimates based on graded color strips or wheels range from 30,000 to 10 million. Tremendous variation exists for differentiating colors and color hues between different individuals. However, when being shown different colors and color hues in isolation, recognition of differences quickly drops significantly. In addition, sex, age, certain disease states, and lifestyle choices can have an effect on the ability to see and distinguish colors. In comparison, a 12-bit camera can accurately and independently distinguish 68 billion colors.

The perceived color is known to depend not only on the spectral distribution of the light reflected by that particular color, but also on the light nearby. This phenomenon is called chromatic or color induction, and is composed of two components: color contrast and color assimilation. Color contrast presents itself as follows: yellow light will appear yellow (580 nm wavelength) when viewed independently of other colors, but will appear as a green hue when it is surrounded by red (670 nm wavelength). Color assimilation occurs when the color appearance shifts away from the appearance of the nearby light, whereas the latter occurs when the appearance shifts towards the color of the inducing light. Color assimilation has been demonstrated in several situations, including the watercolor effect. In the watercolor effect, two uneven, colored contours, one darker than the other, surrounding an uncolored space results in the uncolored area appearing to take on the lighter color. For example, when a white space is surrounded by an orange inner and purple outer boarder, the enclosed white area appears to be orange-tinged.

In practical terms, these color phenomena may impact efforts to score the level of cytoplasmic staining in the context of adjacent membrane staining of different hues, or vice versa. Variability in color hue recognition may also impact the evaluation of multi-color bright-field staining (e.g., multiplex immunohistochemistry) where one must differentiate colors and color hues that are in close proximity or co-localized.

Lateral inhibition is an optical effect resulting in altered color perception arising from neuronal interference in the retina and optical tracts. For example, the Hermann grid illusion results in perception of false points at inflection points between interfaces of light and dark lines and squares forming a grid. This occurs when excited neurons reduce the activity of their neighbors to prevent the spread of action potentials in a lateral direction. When looking at a light edge next to a dark edge, lateral inhibition makes the light edge appear even lighter, because the inhibition from neighboring neurons activated by the darker edge have a smaller inhibitory effect than a light region surrounded by a light border. Similarly, the dark border next to the light border is perceived as even darker. This results in an increase in the perceived contrast and sharpness of images at the "cost" of viewing certain things as lighter or darker than they actually are.

In addition, so called "forbidden colors" are composed of pairs of hues whose light frequencies automatically cancel each other out. These color combinations are supposed to be impossible to see simultaneously, although research has shown that training can enable certain observers to see these "forbidden colors".

It is known that there are differences in color vision and perception between men and women, or in general among individuals due to different genetic makeups.

Similarly, the minimum saturation of a color that can still be recognized by human vision varies amongst individuals, and is strongly influenced by other factors, such as light intensity in the field of vision (e.g., day vs. night), light source (e.g., sunlight vs. fluorescent light), context in which the color is shown, and if the color is shown in isolation or in combination of other colors. Taken together, these factors introduce a large amount of variability in perception of colors, especially at low saturation levels.

SUMMARY

This disclosure aims at not only detecting staining intensities at or below the general threshold of human color and saturation perception, but also defines a tool to minimize intra- and inter-observer variability to generate more reproducible and consistent data.

In accordance with the embodiments herein, methods are described for extracting information from patient tissue samples with immunostaining that is at a level that is below the threshold of visual perception. Digital image analysis algorithms are utilized to extract information from digital images of patient tissue samples that have been assayed with both a tissue-based test and a control. The information extracted from the digital images of the control is used to set a baseline threshold of immunostaining for the patient. This baseline threshold is then used, in combination with the information extracted from the tissue-based test images, to calculate a patient-specific biomarker score for the patient, where the patient-specific biomarker score cannot be generated by visual assessment of the tissue sample. The patient-specific biomarker score is then used to assess the patient status.

DETAILED DESCRIPTION OF EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

For purpose of definition, a tissue object is one or more of a cell (e.g., immune cell), cell sub-compartment (e.g., nucleus, cytoplasm, membrane, organelle), cell neighborhood, a tissue compartment (e.g., tumor, tumor microenvironment (TME), stroma, lymphoid follicle, healthy tissue), blood vessel, and a lymphatic vessel. Tissue objects are visualized by histologic stains which highlight the presence and localization of a tissue object. Tissue objects can be identified directly by stains specifically applied to highlight said tissue object (e.g., hematoxylin to visualize nuclei, IHC stain for a protein specifically found in a muscle fiber membrane), indirectly by stains applied which non-specifically highlight the tissue compartment (e.g., DAB background staining), or are biomarkers known to be localized to a specific tissue compartment (e.g., nuclear-expressed protein, carbohydrates only found in the cell membrane).

For the purpose of this disclosure, patient status includes diagnosis of disease state, disease severity, disease progression, and therapy efficacy. Other patient statuses are contemplated.

In an illustrative embodiment of the invention, the method generally comprises seven steps, including: (i) staining a first tissue section originating from a patient, the first tissue section stained with a tissue-based test, (ii) applying a control staining process to a second tissue section from the same patient, (iii) applying a control algorithm to an image of the control tissue section to set a control threshold, (iv) modifying the control algorithm with the control threshold to create an analysis algorithm, (v) applying the analysis algorithm to a digital image of the stained first tissue section to extract a dataset that associates a quantity of the biomarker or biomarkers of interest at a specific location in a tissue object in the first stained tissue section, (vi) calculating a patient-specific biomarker score from the dataset, where the patient-specific biomarker score cannot be generated by visual assessment of the stained tissue sample, and (vii) determining a patient status for the patient based on the patient-specific biomarker score.

Using the illustrative embodiment, a plurality of tissue sections from the same patient may be similarly processed and analyzed.

Figure 1:
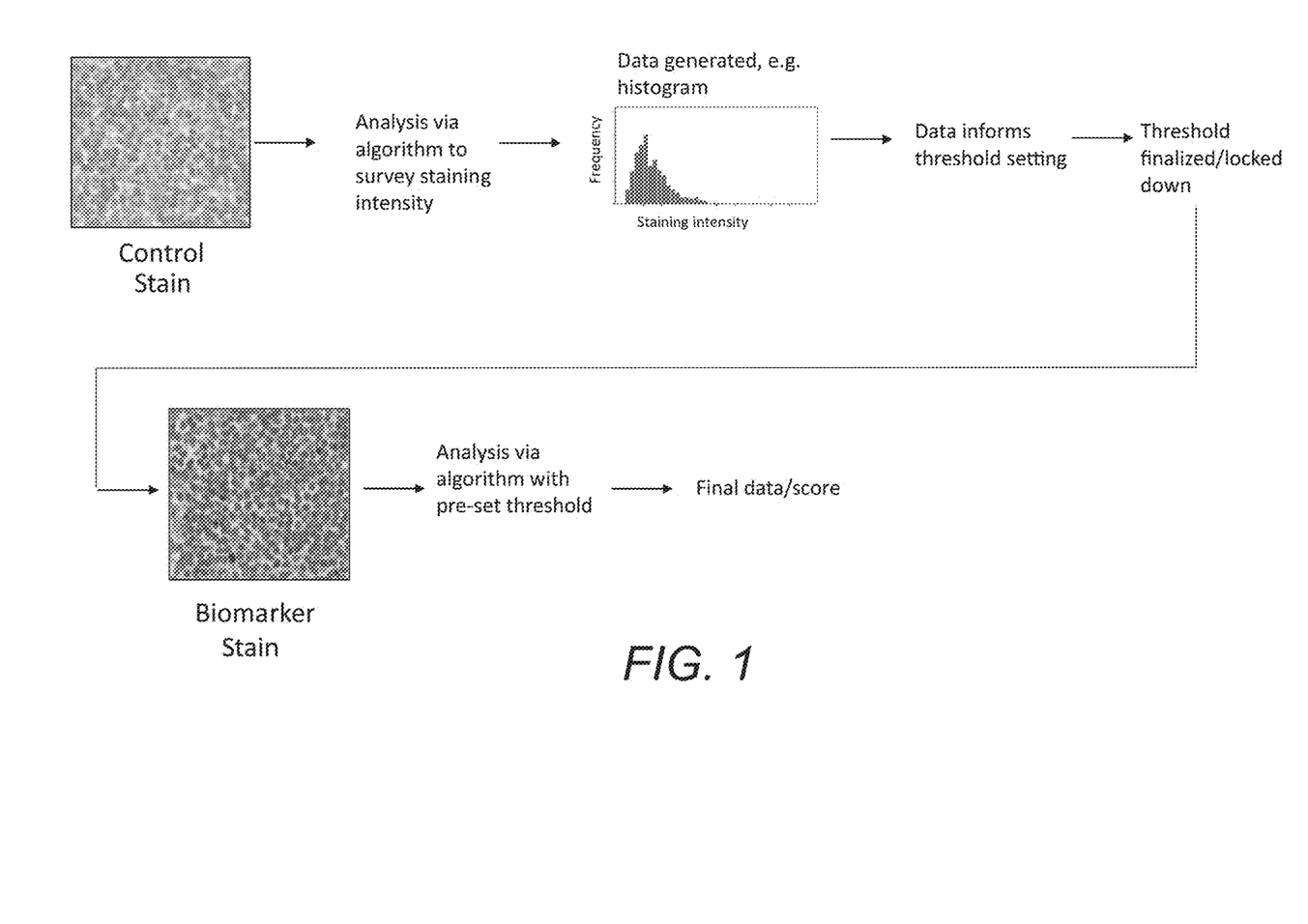
FIG. 1 outlines a process in which a control slide is analyzed via an algorithm to survey staining intensities of all cells analyzed; this data is used to inform threshold settings to analyze biomarker stained slides from the same patient sample via an algorithm; the result of this analysis yields the final data or final score for this patient sample.

FIG. 1 outlines an example of a process configured to arrive at a patient status based on detection of immunostaining that is below the threshold of visual perception. In this embodiment, a patient's tissue is prepared in a microscope or similar slide as a first tissue section and a second tissue section, the first tissue section is stained with an immunohistochemical ("IHC") staining process and the second tissue section is stained with a control staining process. A first digital image is acquired for the first tissue section (IHC section), and a second digital image is acquired for the second tissue section (control). A control algorithm process is then applied to the second digital image to generate a control threshold. The control algorithm is then modified with the control threshold to generate an analysis algorithm. The analysis algorithm is then applied to the first digital image (IHC section) to generate a dataset that associates a quantity of a specific analyte or biomolecule at a specific location in a tissue object in the first tissue section and the biomarker staining levels are at or below the threshold of human visual perception. The dataset is used to derive a patient-specific biomarker score. Therefore, said the patient-specific biomarker score cannot be generated by visual means. Finally, patient status is assessed based on the patient-specific biomarker score.

The process may be repeated for multiple IHC-stained first tissue sections using the same or multiple controls, and data combined using a mathematical operation.

Additionally, this embodiment can be practiced with immunofluorescence ("IF") staining instead of IHC staining.

The typical control method used with this embodiment are isotype controls, although other methods for control are acceptable. Isotype controls allow for the incidental staining from non-specific biomarkers, in both IHC and IF, to be controlled for. Isotype controls use the same staining protocol as the biomarker staining, however, the primary target detection reagent is removed and replaced either with diluent only, a monoclonal antibody of the same species and concentration for a target not present in the slide, or a polyclonal antibody mixture of the same species and overall concentration that does not contain antibodies specific for the biomarker target.

In a further embodiment of this method, the threshold set using the control algorithm may be such that it is below the threshold of visual perception.

Figure 2:
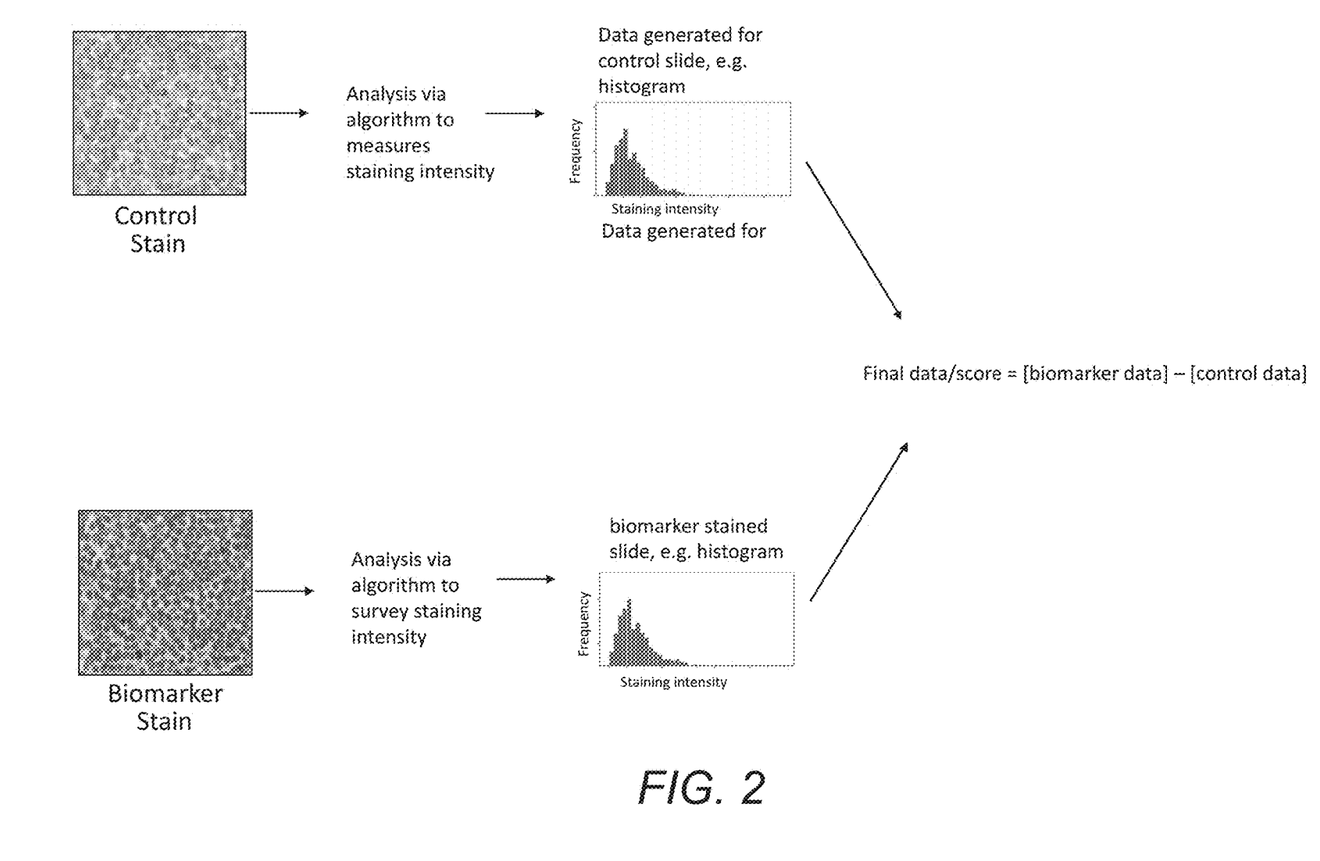
FIG. 2 outlines a process in which both control and biomarker stained slides from the same patient sample are analyzed via an algorithm to survey staining intensities of all cells analyzed; this data from both slides is used to calculate final data or a final score for this patient sample.

FIG. 2 shows another embodiment, wherein a patient's tissue is sectioned and stained with each of a control staining process and a biomarker staining process. Digital images are then acquired for both the control and the biomarker sections to produce at least one first image (biomarker staining) and at least one second image (control). The same algorithm is then used to analyze the digital images of both the biomarker and control sections, i.e. first and second images, respectively. A control dataset and a biomarker dataset are generated from the algorithm analysis of the first and second digital images, where both datasets associate a quantity of a specific analyte or biomolecule at a specific location in a tissue object in the respective tissue section. The datasets are then mathematically manipulated to generate a patient-specific biomarker score, where the patient-specific biomarker score is below the threshold of visual perception. Finally, the patient status is assessed based on the patient-specific biomarker score.

In this embodiment, both IHC and IF biomarker staining can be used to express the localization of biomarkers in the biomarker tissue.

The typical control method used for this embodiment is isotype control, although other methods of control are contemplated.

Figure 3:
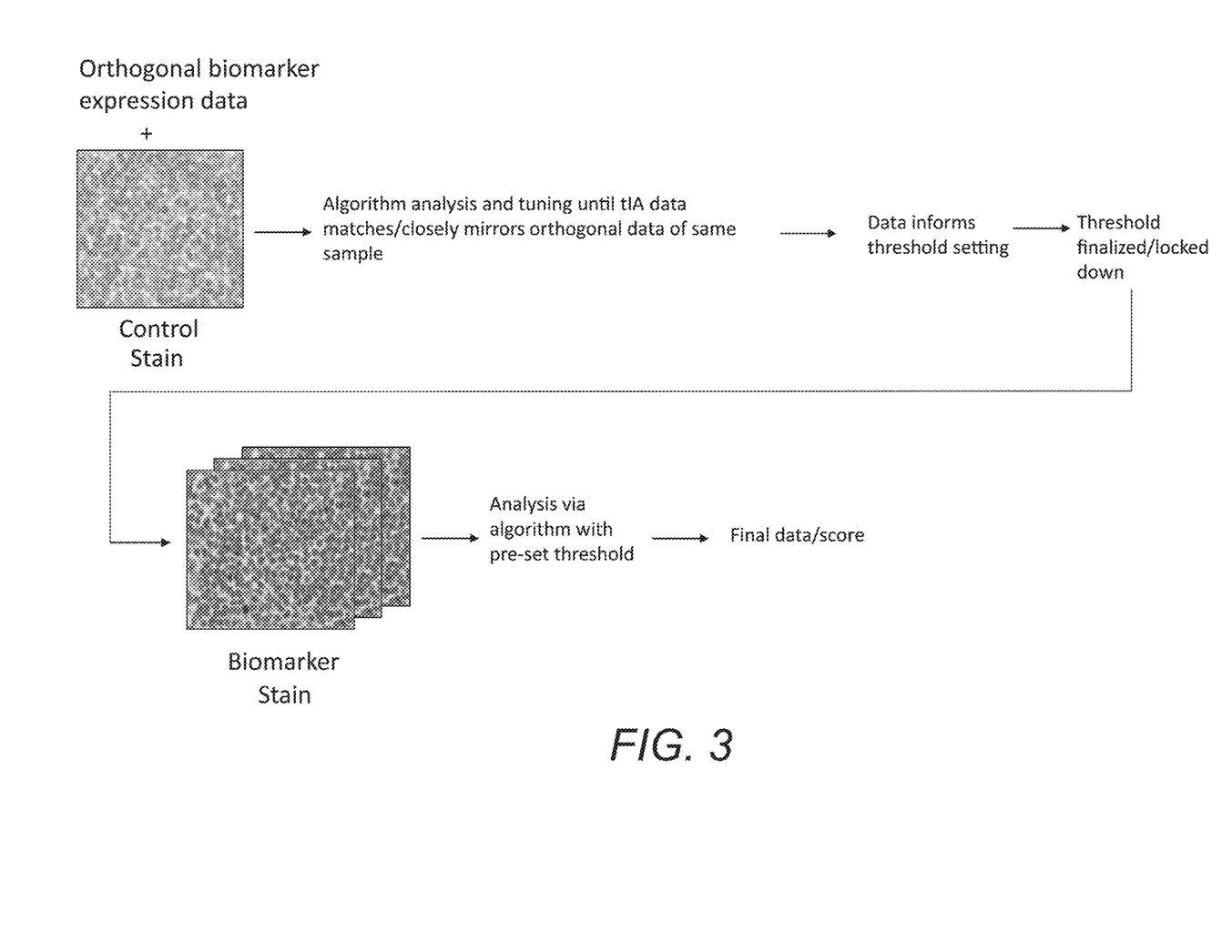
FIG. 3 outlines a process in which orthogonal biomarker expression data is used in the analysis of a control slide to inform algorithm development, tuning, and threshold setting; the algorithm with a finalized threshold is used to analyze biomarker stained slides individually, and the resulting data is the final data or final score for each sample.

In an alternative embodiment of the invention, orthogonal biomarker expression data is used to set the threshold that is used to modify the analysis algorithm. FIG. 3 illustrates a method that follows this embodiment. As shown in FIG. 3, a patient's tissue sections are stained to produce at least one first tissue section including an IHC or IF staining process and at least one second tissue section including a control staining process. First and second digital images are then acquired for the stained section(s) and the control section(s), respectively. Then, a control algorithm is modified until the control algorithm produces data from the control image that is equivalent to the orthogonal biomarker expression data. The control threshold is then used to modify an analysis algorithm. The modified analysis algorithm is then used to analyze the stained sections to generate a dataset that associates a quantity of a specific analyte or biomolecule at a specific location in a tissue object in the tissue section, and the biomarker staining levels are at or below the threshold of human visual perception. The dataset is used to derive a patient-specific biomarker score. Therefore, said the patient-specific biomarker score cannot be generated by visual means. Finally, the patient status is assessed based on the patient-specific biomarker score.

In this embodiment, the typical orthogonal biomarker expression data is data from flow cytometry, but other orthogonal biomarker expression data are contemplated. The typical control staining process used with this embodiment is isotype control, but other control staining processes are contemplated.

Figure 4:
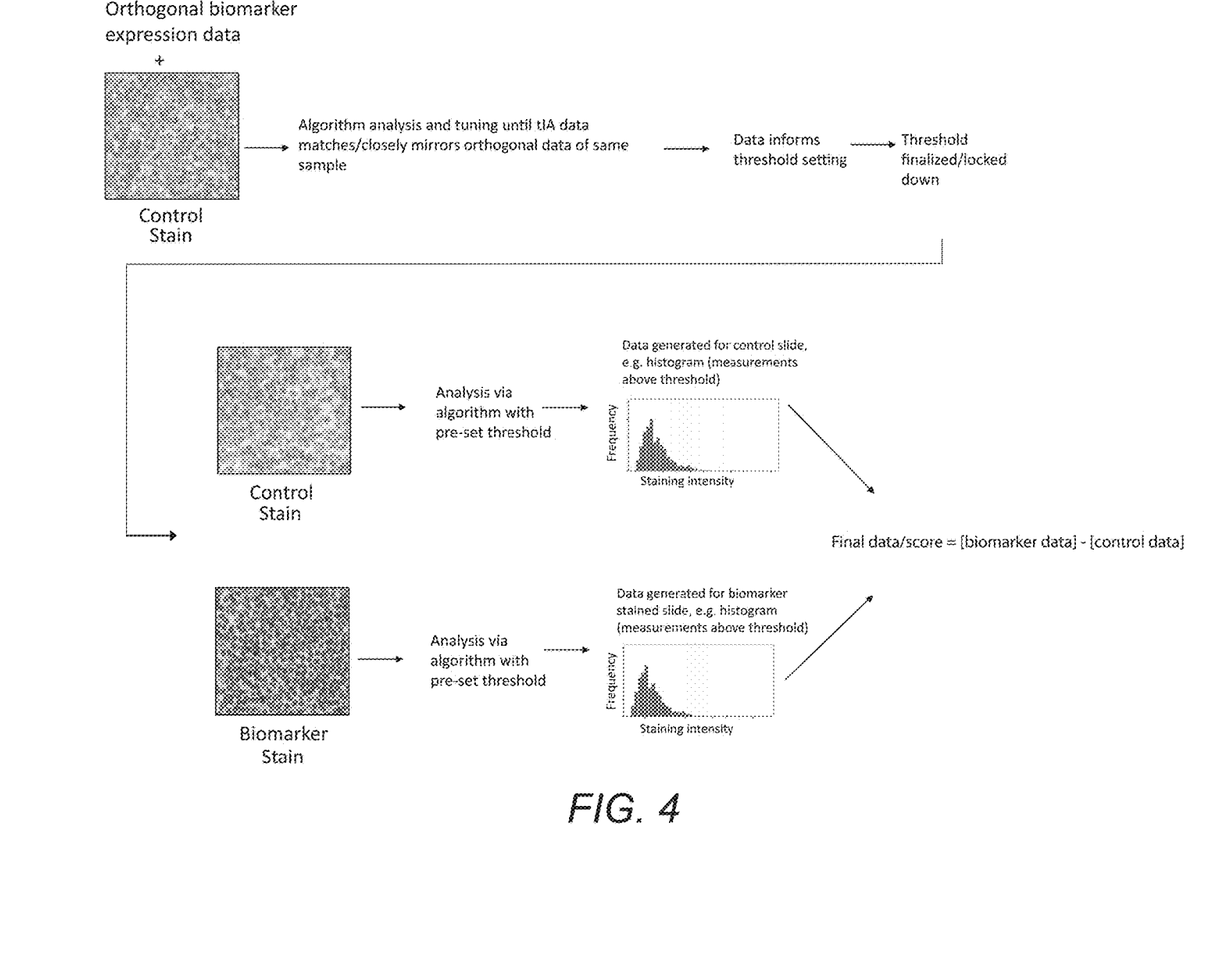
FIG. 4 outlines a process in which orthogonal biomarker expression data is used in the analysis of a control slide to inform algorithm development, tuning, and threshold setting; the algorithm with a finalized threshold is used to analyze both the control as well as the biomarker stained slide (both from the same patient sample), and the resulting data from both slides is used to calculate final data or a final score for this patient sample.

FIG. 4 shows a further embodiment of the invention in which a patient's tissue sections are stained with both a control and a biomarker staining process. Digital images of both the control section and the biomarker section are acquired. Then, an algorithm process is modified until the algorithm process produces data from the control image that is equivalent to orthogonal biomarker expression data. This modified algorithm process is then used to establish a threshold which is used to analyze both the control image and the biomarker image. This analysis creates a control dataset and a biomarker dataset, where both datasets associate a quantity of a specific analyte or biomolecule at a specific location in a tissue object in the respective tissue section. The datasets are then mathematically manipulated to generate a patient-specific biomarker score, where the patient-specific biomarker score is below the threshold of visual perception. Finally, the patient status is assessed based on the patient-specific biomarker score.

In this embodiment, the typical orthogonal biomarker expression data is from flow cytometry, but other orthogonal biomarker expression data are contemplated. The typical control staining process used with this embodiment is isotype control, but other control staining processes are contemplated.

In another embodiment of the invention, a patient's tissue section is stained with a biomarker stain. Digital images of the biomarker section are acquired. Then, an algorithm process is modified with a threshold using orthogonal biomarker expression data. This modified algorithm process is then used to analyze the biomarker image. This analysis creates a dataset, where the dataset associates a quantity of a specific analyte or biomolecule at a specific location in a tissue object in the respective tissue section. The dataset is used to generate a patient-specific biomarker score, where the patient-specific biomarker score is below the threshold of visual perception. Finally, the patient status is assessed based on the patient-specific biomarker score. This embodiment is encapsulated in FIG. 5.

Figure 5:
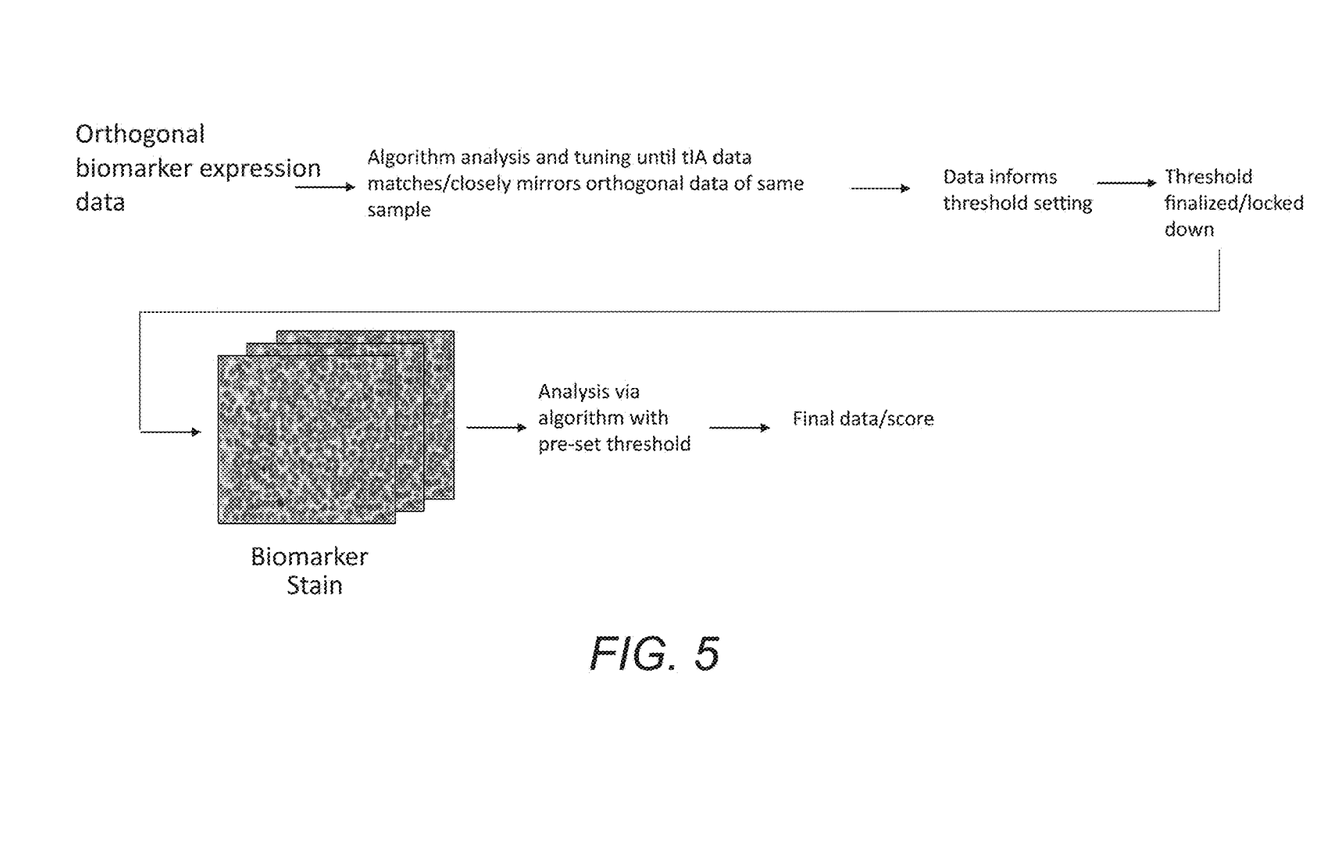
FIG. 5 outlines a process in which orthogonal biomarker expression data is used to inform algorithm development, tuning, and threshold setting; the algorithm with a finalized threshold is used to analyze patient's biomarker stained slides, and the resulting data is the final data or final score for each sample.

In this embodiment, orthogonal biomarker expression data includes data generated from xenograft tissue samples harvested from mouse or other species containing human cells, and samples of known biomarker expression. Other methods of generating orthogonal biomarker expression data are contemplated.

Figure 6:
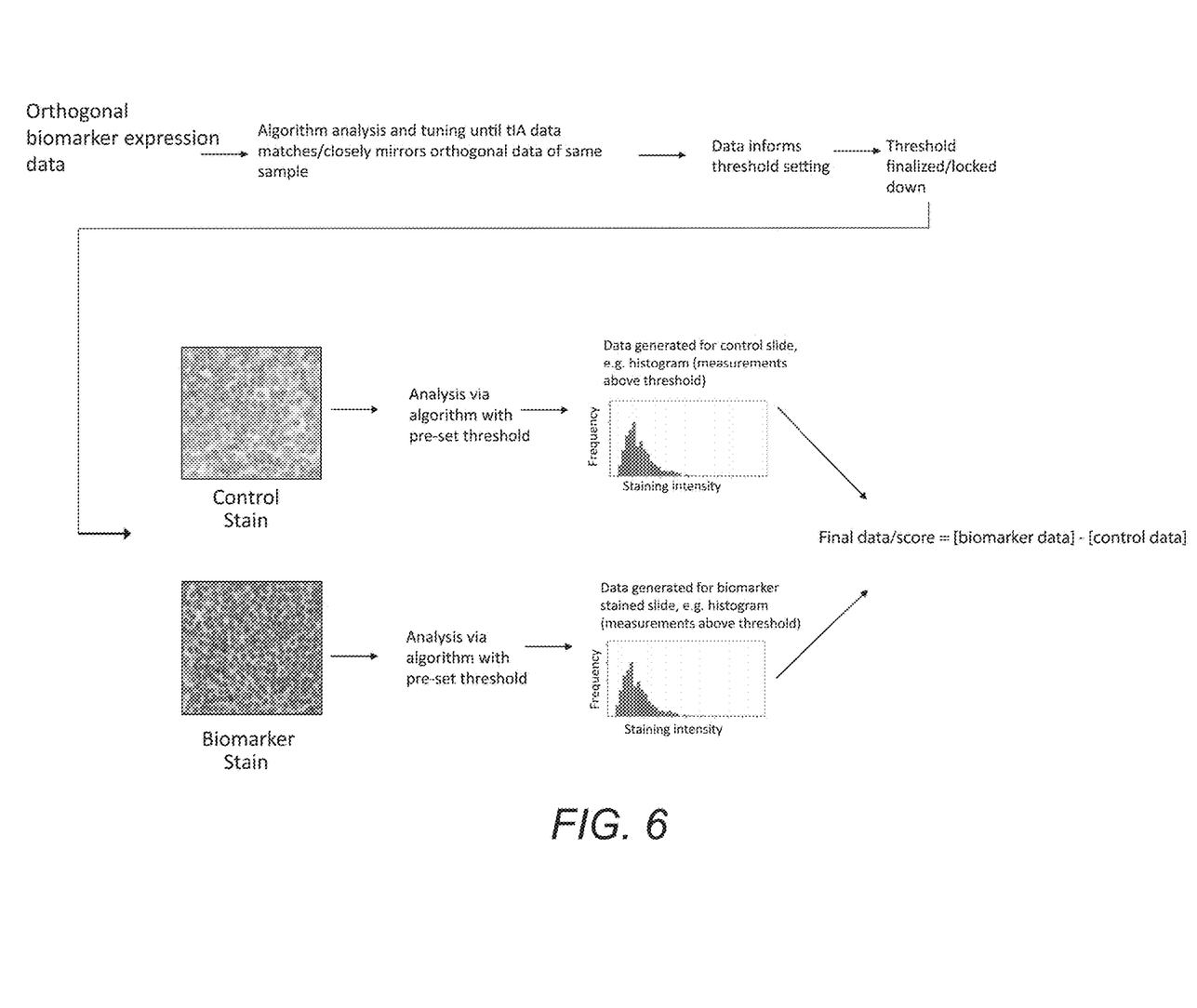
FIG. 6 outlines a process in which orthogonal biomarker expression data is used to inform algorithm development, tuning, and threshold setting; the algorithm with a finalized threshold is used to analyze both the patient's control as well as the biomarker stained slide, and the resulting data from both slides is used to calculate final data or a final score for this patient sample.

In an additional embodiment of the invention, as shown in FIG. 6, a patient's tissue sections are stained with both a control and a biomarker staining process. Digital images of both the control section and the biomarker section are acquired. Then, an algorithm process is modified with a threshold using orthogonal biomarker expression data. This modified algorithm process is then used to establish a threshold which is used to analyze both the control image and the biomarker image. This analysis creates a control dataset and a biomarker dataset, where both datasets associate a quantity of a specific analyte or biomolecule at a specific location in a tissue object in the respective tissue section. The datasets are then mathematically manipulated to generate a patient-specific biomarker score, where the patient-specific biomarker score is below the threshold of visual perception. Finally, the patient status is assessed based on the patient-specific biomarker score.

In this embodiment, orthogonal biomarker expression data includes data generated from xenograft tissue samples harvested from mouse or other species containing human cells, and samples of known biomarker expression. Other methods of generating orthogonal biomarker expression data are contemplated.

Additionally, the embodiments herein described may be used beyond a single patient. A patient cohort can be analyzed via any of the methods embodied above, where a single threshold is set for the entire cohort. The single threshold would then be used for the same algorithm process to analyze the entire cohort, while still generating a dataset that associates a quantity of a specific analyte or biomolecule at a specific location in a tissue object in the tissue section for each patient in the cohort. Each patient's individual dataset is used to derive a patient-specific biomarker score for that patient, where the patient-specific biomarker score is below or at the threshold of visual perception. Finally, the patient status is assessed based on the patient-specific biomarker score.

Furthermore, it is contemplated that multiple control sections, such as slides of known staining intensity, can be used to establish the control threshold for each of the of the embodiments disclosed herein. The additional control sections would not come from the patient for which the stained section is being analyzed, but from a source of known staining intensity.

What is claimed is:

1. A method comprising:
   obtaining a patient's at least one first and at least one second tissue sections;
   using a biomarker staining process to stain the at least one first tissue sections for biomarker expression to generate at least one stained tissue section;
   using a control staining process to stain the at least one second tissue sections with a control to generate at least one control tissue section;
   obtaining at least one digital image of the at least one stained tissue sections and at least one digital image of the at least one control tissue sections;
   modifying an algorithm process until the algorithm process produces data from the at least one digital image of the control tissue section that recapitulates an orthogonal biomarker expression dataset to generate a threshold;
   applying the threshold to the modified algorithm process to generate an analysis algorithm process;
   extracting a first dataset that associates a quantity of the biomarker at a specific location in a tissue object in the stained tissue section from the control tissue section by applying the analysis algorithm process to the at least one digital image of the control tissue section;
   extracting a second dataset that associates a quantity of the biomarker at a specific location in a tissue object in the stained tissue section from the stained tissue section by applying the analysis algorithm process to the at least one digital image of the stained tissue section;
   calculating a patient-specific biomarker score from the first and second datasets, wherein the patient-specific biomarker score cannot be generated by visual assessment of the stained tissue sample; and
   determining at least one patient status for the patient based on the patient-specific biomarker score, wherein the at least one patient status is selected from the group consisting of diagnosis, disease severity, disease progression, therapy candidacy, and therapy efficacy.

2. The method of claim 1, wherein the at least one first and at least one second tissue sections are adjacent tissue sections.

3. The method of claim 1, wherein the biomarker staining process is selected from the group consisting immunohistochemistry and immunofluorescence.

4. The method of claim 1, wherein the control staining process is isotype control.

5. The method of claim 1, wherein the threshold is not above the threshold of visual perception.

6. The method of claim 1, further comprising applying the analysis algorithm to a plurality of patients' digitized stained tissue sections.

7. A method comprising:
   obtaining a patient's at least one first and at least one second tissue sections;
   using a biomarker staining process to stain the at least one first tissue sections for biomarker expression to generate at least one stained tissue sections;
   using a control staining process to stain the at least one second tissue sections with a control to generate at least one control tissue sections;
   obtaining at least one digital image of the at least one stained tissue sections and at least one digital image of the at least one control tissue sections;
   modifying an algorithm process by setting a threshold, wherein the threshold is derived from orthogonal biomarker expression data to generate an analysis algorithm process;
   extracting a first dataset that associates a quantity of the biomarker at a specific location in a tissue object in the stained tissue section from the control tissue section by applying the analysis algorithm process to the at least one digital image of the control tissue section;
   extracting a second dataset that associates a quantity of the biomarker at a specific location in a tissue object in the stained tissue section from the stained tissue section by applying the analysis algorithm process to the at least one digital image of the stained tissue section;
   calculating a patient-specific biomarker score from the first and second datasets, wherein the patient-specific biomarker score cannot be generated by visual assessment of the stained tissue sample; and
   determining at least one patient status for the patient based on the patient-specific biomarker score, wherein the at least one patient status is selected from the group consisting of diagnosis, disease severity, disease progression, therapy candidacy, and therapy efficacy.

8. The method of claim 7, wherein the at least one first and at least one second tissue sections are adjacent tissue sections.

9. The method of claim 7, wherein the first staining process is selected from the group consisting immunohistochemistry and immunofluorescence.

10. The method of claim 7, wherein the control staining process is isotype control.

11. The method of claim 7, wherein the threshold is not above the threshold of visual perception.

12. The method of claim 7, further comprising applying the analysis algorithm to a plurality of patients' digitized stained tissue sections.

* * * * *